US007309814B1

(12) United States Patent
Zhang et al.

(10) Patent No.: US 7,309,814 B1
(45) Date of Patent: Dec. 18, 2007

(54) NUCLEIC ACID MOLECULES ENCODING BACTERIAL AUTOINDUCER INACTIVATION PROTEIN AS TARGETS FOR ENGINEERING DISEASE RESISTANCE

(75) Inventors: Lian-Hui Zhang, Singapore (SG); Yihu Dong, Singapore (SG); Jinling Xu, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 0 days.

(21) Appl. No.: 10/019,661

(22) PCT Filed: Nov. 17, 1999

(86) PCT No.: PCT/SG99/00128

§ 371 (c)(1),
(2), (4) Date: Apr. 29, 2002

(87) PCT Pub. No.: WO01/02578

PCT Pub. Date: Jan. 11, 2001

(30) Foreign Application Priority Data

Jul. 2, 1999 (SG) .................................. 9903146-0

(51) Int. Cl.
*C12N 15/82* (2006.01)
*C12N 15/31* (2006.01)
*C12N 1/21* (2006.01)

(52) U.S. Cl. .................. 800/279; 424/93.2; 435/320.1; 536/23.7

(58) Field of Classification Search ................ 800/279; 536/23.7, 23; 424/93.2; 435/6
See application file for complete search history.

(56) References Cited

U.S. PATENT DOCUMENTS 5,591,872 A    1/1997  Pearson et al.
5,993,827 A *  11/1999  Sim et al. ................ 424/268.1

FOREIGN PATENT DOCUMENTS

WO       WO95/33818 A2    12/1995

OTHER PUBLICATIONS

Lazar et al, 1988, Mol. Cell. Biol. 8:1247-1252.*
Hill et al, 1998, Biochem. Biophys. Res. Comm. 244:573-577.*
Molin et al, 2003, FEMS Microbiol. Ecol. 45:71-81.*
Zhang, 2003, Trends Plant Sci. 8:238-244.*
Guo et al, 2004, Proc. Natl. Acad. Sci. USA 101: 9205-9210.*
Luo et al., The Antiactivatior TraM Interferes with the Autoinducer-dependent Binding of TraR to DNA by Interacting with the C-terminal Region of the Quorum-sensing Activator, The Journal of Biological Chemistry, Mar. 2000, pp. 7713-7722, vol. 275, No. 11, by The American Society for Biochemistry and Molecular Biology, Inc., printed in U.S.A.
Hwang et al., A New Regulatory Element Modulates Homoserine Lacton-Mediated Autoinduction of Ti Plasmid Conjugal Transfer, Journal of Bacteriology, Jan. 1995, p. 449-458, vol. 177, No. 2, American Society for Microbiology.

* cited by examiner

*Primary Examiner*—Anne Kubelik
(74) *Attorney, Agent, or Firm*—Rothwell, Figg, Ernst & Manbeck, PC

(57) ABSTRACT

The present invention relates to isolated nucleic acid molecules encoding a bacterial autoinactivation protein and methods for increasing disease resistance and preventing or reducing bacterial damage in plants and animals. The nucleic acid that encodes the bacterial autoinducer inactivation protein can be introduced into a cell so that the bacterial autoinducer inactivation protein is expressed by the plant or animal. The nucleic acid may confer resistance to disease where the expression of pathogenic genes are regulated by autoinducers.

11 Claims, 7 Drawing Sheets

..ctttactgtattgttttattcaaaactaaatgtaaaggtggatacata        -1
ATGACAGTAAAGAAGCTTTATTTCGTCCCAGCAGGTCGTTGTATGTTGGA        50
TCATTCGTCTGTTAATAGTACATTAACACCAGGAGAATTATTAGACTTAC        100
CGGTTTGGTGTTATCTTTTGGAGACTGAAGAAGGACCTATTTTAGTAGAT        150
ACAGGTATGCCAGAAAGTGCAGTTAATAATGAAGGTCTTTTTAACGGTAC        200
ATTTGTCGAAGGGCAGGTTTTACCGAAAATGACTGAAGAAGATAGAATCG        250
TGAATATTTTAAAACGGGTTGGTTATGAGCCGGAAGACCTTCTTTATATT        300
ATTAGTTCTCACTTGCATTTTGATCATGCAGGAGGAAATGGCGCTTTTAT        350
AAATACACCAATCATTGTACAGCGTGCTGAATATGAGGCGGCGCAGCATA        450
GCGAAGAATATTTGAAAGAATGTATATTGCCGAATTTAAACTACAAAATC        500
ATTGAAGGTGATTATGAAGTCGTACCAGGAGTTCAATTATTGCATACACC        550
AGGCCATACTCCAGGGCATCAATCGCTATTAATTGAGACAGAAAAATCCG        600
GTCCTGTATTATTAACGATTGATGCATCGTATACGAAAGAGAATTTTGAA        650
AATGAAGTGCCATTTGCGGGATTTGATTCAGAATTAGCTTTATCTTCAAT        700
TAAACGTTTAAAAGAAGTGGTGATGAAAGAGAAGCCGATTGTTTTCTTTG        750
GACATGATATAGAGCAGGAAAGGGGATGTAAAGTGTTCCCTGAATATATA        800
TAGtacaaaaagtcatgagcttattcgctcatgacttttcgtttaaatg        850
Attttttaaataagttataaacttttttagaactatcttcatttaattg        900
Atagtacgtaaggtttacatcattaggagtatcttgttgagcaatcatca        950
Cttcgttactgtgatggtcaactacccatatgaaatattttttataagtc        1000
Ccatcctcgaaagtaatccacatatcacagtctattaaatctgatccttc        1050
Ttcatctaatgttaattttccttttttggcggtatccatactgttaatga        1100
Atgttttaattcatctgttttgtgagaaagatatcctttttgtttta        1150
Attgactcgacatgtatatcttttatttcttgttttcctaaaaagacagg        1200
gggctcatttgggtctctttgagt                                  1222

FIG.4A

MTVKKLYFVPAGRCMLDHSSVNSTLTPGELLDLPVWCYLLETEEGPILVD  50
TGMPESAVNNEGLFNGTFVEGQVLPKMTEEDRIVNILKRVGYEPEDLLYI 100
ISSHLHFDHAGGNGAFINTPIIVQRAEYEAAQHSEEYLKECILPNLNYKI 150
IEGDYEVVPGVQLLHTPGHTPGHQSLLIETEKSGPVLLTIDASYTKENFE 200
NEVPFAGFDSELALSSIKRLKEVVMKEKPIVFFGHDIEQERGCKVFPEYI 250

FIG.4B

Asp: [LIVMFGAC]-[LIVMTADN]-[LIVFSA]-D-[ST]-G-[STAV]-

AiiA:  $I_{47}$         L          V        D  T  G  M

Asp: [STAPDENQ]-X-[LIVMFSTNC]-X-[LIVMFGTA]

AiiA:     P       E      S       A    $V_{58}$

FIG.5

SEQUENCE LISTING

<160> NUMBER OF SEQ ID NOS: 4

<210> SEQ ID NO 1
<211> LENGTH: 1222
<212> TYPE: DNA
<213> ORGANISM: Bacillus sp.

<400> SEQUENCE: 1

```
ctttactgta ttgttttatt caaaactaaa tgtaaaggtg gatacataat gacagtaaag      60
aagctttatt tcgtcccagc aggtcgttgt atgttggatc attcgtctgt taatagtaca     120
ttaacaccag gagaattatt agacttaccg gtttggtgtt atcttttgga gactgaagaa     180
ggacctattt tagtagatac aggtatgcca gaaagtgcag ttaataatga aggtcttttt     240
aacggtacat ttgtcgaagg gcaggtttta ccgaaaatga ctgaagaaga tagaatcgtg     300
aatattttaa aacgggttgg ttatgagccg gaagaccttc tttatattat tagttctcac     360
ttgcattttg atcatgcagg aggaaatggc gcttttataa atacaccaat cattgtacag     420
cgtgctgaat atgaggcggc gcagcatagc gaagaatatt tgaaagaatg tatattgccg     480
aatttaaact acaaaatcat tgaaggtgat tatgaagtcg taccaggagt tcaattattg     540
catacaccag gccatactcc agggcatcaa tcgctattaa ttgagacaga aaaatccggt     600
cctgtattat taacgattga tgcatcgtat acgaaagaga attttgaaaa tgaagtgcca     660
tttgcgggat ttgattcaga attagcttta tcttcaatta aacgtttaaa agaagtggtg     720
atgaaagaga agccgattgt tttctttgga catgatatag agcaggaaag gggatgtaaa     780
gtgttccctg aatatatata gtacaaaaag tcatgagctt attcgctcat gactttttcg     840
tttaaatgat ttttttaaat aagttataaa ctttttttaga actatcttca tttaattgat     900
agtacgtaag gtttacatca ttaggagtat cttgttgagc aatcatcact tcgttactgt     960
gatggtcaac tacccatatg aaatattttt tataagtccc atcctcgaaa gtaatccaca    1020
tatcacagtc tattaaatct gatccttctt catctaatgt taattttcct tttttggcgg    1080
tatccatact gttaatgaat gttttttaatt catctgtttt tgtgagaaag atatccttt    1140 ttgttttaat tgactcgaca tgtatatctt ttatttcttg ttttcctaaa aagacagggg    1200
gctcatttgg gtctctttga gt                                             1222
```

```
<210> SEQ ID NO 2
<211> LENGTH: 250
<212> TYPE: PRT
<213> ORGANISM: Bacillus sp.

<400> SEQUENCE: 2

Met Thr Val Lys Lys Leu Tyr Phe Val Pro Ala Gly Arg Cys Met Leu
1               5                   10                  15

Asp His Ser Ser Val Asn Ser Thr Leu Thr Pro Gly Glu Leu Leu Asp
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Val Leu Pro Lys Met Thr Glu Glu
65              70                  75                  80

Asp Arg Ile Val Asn Ile Leu Lys Arg Val Gly Tyr Glu Pro Glu Asp
                85                  90                  95

Leu Leu Tyr Ile Ile Ser Ser His Leu His Phe Asp His Ala Gly Gly
            100                 105                 110

Asn Gly Ala Phe Ile Asn Thr Pro Ile Ile Val Gln Arg Ala Glu Tyr
        115                 120                 125

Glu Ala Ala Gln His Ser Glu Glu Tyr Leu Lys Glu Cys Ile Leu Pro
    130                 135                 140

Asn Leu Asn Tyr Lys Ile Ile Glu Gly Asp Tyr Glu Val Val Pro Gly
145                 150                 155                 160

Val Gln Leu Leu His Thr Pro Gly His Thr Pro Gly His Gln Ser Leu
                165                 170                 175

Leu Ile Glu Thr Glu Lys Ser Gly Pro Val Leu Leu Thr Ile Asp Ala
            180                 185                 190

Ser Tyr Thr Lys Glu Asn Phe Glu Asn Glu Val Pro Phe Ala Gly Phe
        195                 200                 205

Asp Ser Glu Leu Ala Leu Ser Ser Ile Lys Arg Leu Lys Glu Val Val
    210                 215                 220

Met Lys Glu Lys Pro Ile Val Phe Phe Gly His Asp Ile Glu Gln Glu
225                 230                 235                 240

Arg Gly Cys Lys Val Phe Pro Glu Tyr Ile
                245                 250

<210> SEQ ID NO 3
<211> LENGTH: 12
<212> TYPE: PRT
<213> ORGANISM: Bacillus sp.

<400> SEQUENCE: 3

Ile Leu Val Asp Thr Gly Met Pro Glu Ser Ala Val
1               5                   10

<210> SEQ ID NO 4
<211> LENGTH: 12
<212> TYPE: PRT
<213> ORGANISM: artificial
<220> FEATURE:
<223> OTHER INFORMATION: consensus aspartyl proteases active site motif
<220> FEATURE:
<221> NAME/KEY: MISC_FEATURE
<222> LOCATION: (1)..(1)
<223> OTHER INFORMATION: X= LIVMFGA or C
<220> FEATURE:
```

```
-continued

<221> NAME/KEY: MISC_FEATURE
<222> LOCATION: (2)..(2)
<223> OTHER INFORMATION: X= LIVMTAD or N
<220> FEATURE:
<221> NAME/KEY: MISC_FEATURE
<222> LOCATION: (3)..(3)
<223> OTHER INFORMATION: X= LIVFS or A
<220> FEATURE:
<221> NAME/KEY: MISC_FEATURE
<222> LOCATION: (5)..(5)
<223> OTHER INFORMATION: X= S or T
<220> FEATURE:
<221> NAME/KEY: MISC_FEATURE
<222> LOCATION: (7)..(7)
<223> OTHER INFORMATION: X= STA or V
<220> FEATURE:
<221> NAME/KEY: MISC_FEATURE
<222> LOCATION: (8)..(8)
<223> OTHER INFORMATION: X= STAPDEN or Q
<220> FEATURE:
<221> NAME/KEY: MISC_FEATURE
<222> LOCATION: (9)..(9)
<223> OTHER INFORMATION: X= any amino acid
<220> FEATURE:
<221> NAME/KEY: MISC_FEATURE
<222> LOCATION: (10)..(10)
<223> OTHER INFORMATION: X= LIVMFSTN or C
<220> FEATURE:
<221> NAME/KEY: MISC_FEATURE
<222> LOCATION: (11)..(11)
<223> OTHER INFORMATION: X= any amino acid
<220> FEATURE:
<221> NAME/KEY: MISC_FEATURE
<222> LOCATION: (12)..(12)
<223> OTHER INFORMATION: X= LIVMFGT or A

<400> SEQUENCE: 4

Xaa Xaa Xaa Asp Xaa Gly Xaa Xaa Xaa Xaa Xaa Xaa
1               5                   10
```

NUCLEIC ACID MOLECULES ENCODING BACTERIAL AUTOINDUCER INACTIVATION PROTEIN AS TARGETS FOR ENGINEERING DISEASE RESISTANCE

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to global regulators of bacterial pathogenic genes, and their use to confer disease resistance.

2. Description of the Related Art

A bibliography follows at the end of the Detailed Description of the Invention. The listed references are all incorporated herein by reference.

Cell-to-cell communication via small signal molecules is not only of vital importance to multi-celled living organisms such as animals and plants, it also plays important roles in the functional co-ordination among family members of single-celled organisms like bacteria. Rapid progress over the last few years has clearly established that N-acyl-homoserine lactones, known as autoinducers (AIs), are widely conserved signal molecules in Gram-negative bacteria. AIs were first found in marine bacteria *Vibrio* species in regulation of bioluminescence (Eberhard, et al., 1981; Cao and Meighen, 1989). In recent years, AIs have been identified in a wide range of Gram-negative bacteria. It has been found that AIs are involved in the regulation of a range of biological functions, including Ti plasmid conjugal transfer in *Agrobacterium tumefaciens* (Zhang, et al., 1993), induction of virulence genes in *Erwinia carotovora, Pseudomonas aeruginosa, Erwinia stewartii, Xenorhabdus nematophilus, Erwinia chrysanthemi, Pseudomonas solanacerum*, and *Xanthomonas campestris* (Jones, et al., 1993; Passador, et al., 1993; Pirhonen, et al., 1993; Pearson, et al., 1994; Beck von Bodman and Farrand, 1995; Barber, et al., 1997; Clough, et al., 1997; Costa and Loper, 1997; Dunphy, et al., 1997; Nasser, et al., 1998), regulation of antibiotics production in *Pseudomonas aureofaciens* and *Erwinia carotovora* (Pierson, et al., 1994; Costa and Loper, 1997), regulation of swarming motility in *Serratia liquifaciens* (Eberl, et al., 1996), and biofilm formation in *Pseudomonas fluorescens* and *P. aeruginosa* (Allison, et al., 1998; Davies, et al., 1998). Many more bacterial species are known to produce AIs but the biological functions related have not been established yet (Bassler, et al., 1997; Dumenyo, et al., 1998; Cha, et al., 1998).

Different bacterial species could produce different AIs. All AI derivatives share identical homoserine lactone moieties but can differ in the length and the structure of their acyl groups. The key components in AI-mediated gene regulation systems are LuxI and LuxR type proteins. It has been established now that LuxI-type protein serves as an autoinducer synthase that utilizes acyl-ACPs and AdoMet (S-adenosylmethionine) as substrates (More, et al., 1996; Schaefer, et al., 1996). LuxR-type protein is proposed to be both a receptor for AIs and a AI-dependent transcriptional regulator that binds DNA immediately upstream of the lux promoter (Meighen, 1994; Sitnikov, et al., 1995). A 20-nucleotide inverted repeat has been identified which is centered 44 nucleotides upstream of the transcription start site of the luminescence operon. This sequence called lux box is required for transcriptional activation by LuxR and is probably the LuxR binding site (Fuqua, et al., 1994). Similar 18-bp tra boxes are found upstream of at least three TraR-regulated promoters, and disruption of these elements abolishes transcriptional activation by TraR (Fuqua and Winans, 1996a).

LuxR-type proteins appear to be composed of two modules (Choi and Greenberg, 1991; Hanzelka and Greenberg, 1995). Their carboxyl terminal regions contain a conserved short sequence of 19-amino acid, putative probe-type helix-turn-helix motif, predicted to be involved in binding to target promoters. A general mechanism of activation has been proposed by which the N-terminal domain of LuxR-type protein acts negatively to prevent an interaction between its C-terminal domain and the target DNA binding sites. This inhibition can be relieved by the action of an autoinducer ligand. A strong piece of evidence is that deletion of the N-terminal domain of LuxR results in constitutively active alleles of luxR, whereas larger deletions that remove part of the predicted DNA binding domain abolish transcriptional activation (Choi and Greenberg, 1991). However, other members might use different mechanisms. Recent genetic studies indicate that EsaR and ExpR are likely to be repressors of their target genes rather than activators. Expression of the genes that are repressed by EsaR and ExpR is increased by autoinducers (Beck von Bodman and Farrand 1995; Throup, et al. 1995). It appears that binding of these proteins to their target sites in promoter region causes repression, therefore autoinducer ligands may act to reduce binding affinity.

Evidence that the autoinducer binding site resides in the amino terminal domain of the LuxR protein has been presented (Hanzelka and Greenberg, 1995). LuxR alleles that have mutated amino terminal region require higher level of this signal that does the wild type, indicating this region required for ligand interaction (Slock, et al., 1990; Shadel, et al., 1990). This region (aa 79-127) and a region within the DNA-binding domain (aa 180-230) show a higher degree of conservation among LuxR and its homologs (ca 50% identity) than other parts of these polypeptides. However, the proposed protein-ligand interaction between LuxR and autoinducer has not been proved yet. Analysis of merodiploid *E. coli* strains containing wild-type and mutant LuxR alleles suggested that LuxR functions as a homomultimer and that a region required for multimerization resides within amino acid residues 116 and 161 (Choi and Greenberg, 1992).

BRIEF SUMMARY OF THE INVENTION

In one aspect, the present invention relates to an isolated nucleic acid molecule encoding a bacterial autoinducer inactivation protein.

In another aspect, the present invention relates to a expression vector which comprises a nucleic acid molecule encoding a bacterial autoinducer inactivation protein, wherein the expression vector propagates in a procaryotic or eucaryotic cell.

In yet another aspect, the present invention relates to a cell of a prokaryote or eukaryote transformed or transfected with the expression vector of the present invention.

In yet another aspect, the present invention relates to an isolated protein which has bacterial autoinduction inactivation activity, where the protein comprises the amino acid sequence of SEQ ID NO: 2.

In yet another aspect, the present invention relates to a method for increasing disease resistance in a plant or animal, which method comprises introducing into a cell of such plant or animal a nucleic acid sequence which encodes a bacterial autoinducer inactivation protein in a manner which allows said cell to express said nucleic acid sequence.

In yet another aspect, the present invention relates to a method of preventing or reducing bacterial damage to a plant or animal, which method comprises administering to a plant or animal in need of such prevention or reduction an effective amount of a bacterial autoinducer inactivation protein.

In yet another aspect, the present invention relates to a composition for reducing bacterial damage to a plant or animal, which comprises:
  a) an effective amount of a bacterial autoinducer inactivation protein; and
  b) a suitable carrier.

BRIEF DESCRIPTION OF THE DRAWINGS

FIG. 4A shows the nucleotide sequence of the aiiA gene [SEQ ID NO:1]. The potential ribosome binding sequence and −10 promoter element are underlined and double underlined respectively. The coding portion starts at base 1. The putative factor-independent termination site is labeled by a thick underline. FIG. 4B shows the predicted amino acid sequence of the aiiA gene product [SEQ ID NO:2]. A short peptide sequence similar to the aspartyl protease active site consensus motif is underlined.

FIG. 5 shows the best match of amino acids sequence of aiiA gene product (AiiA) (SEQ. ID NO:3) to the consensus aspartyl proteases active site motif (Asp) (SEQ ID NO:4. Symbol: X, any amino acid. A vertical line indicates perfect match.

DETAILED DESCRIPTION OF THE INVENTION

Figure 1:
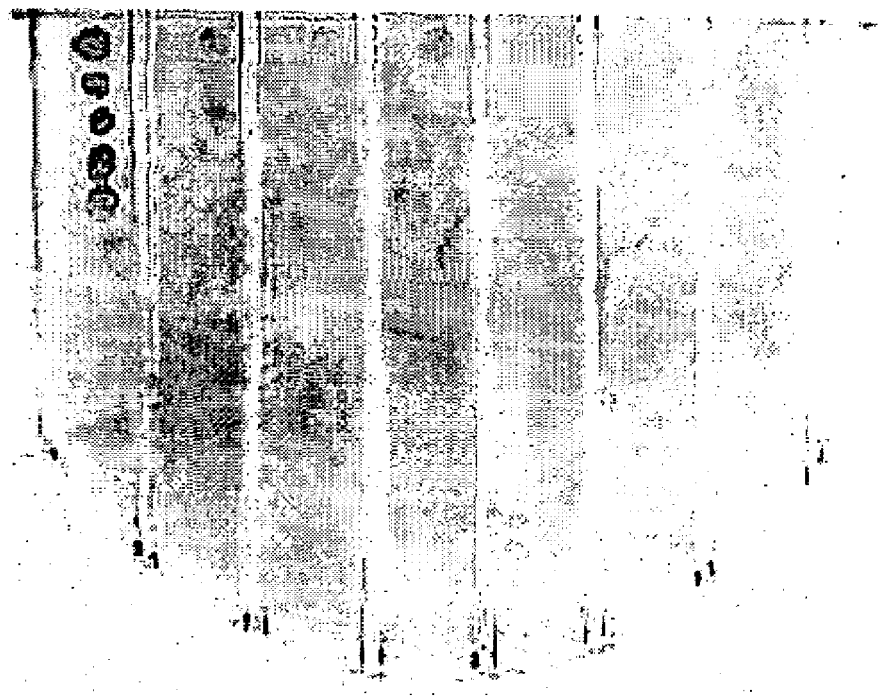
FIG. 1 shows the time course of AIs inactivation by cell extracts from *Bacillus* sp. strain 240BI. Cell extracts in 0.2 M phosphate buffer (pH 7.0) containing 100 ug total protein were added to the same buffer containing OHHL in a final concentration of 20 uM. The reaction was conducted in a 1.5 ml Eppendorf centrifuge tube in a final volume of 200 microliters and incubated at 28° C. Same concentration of OHHL in the phosphate buffer was used as control. Samples were taken at 10-min interval till 60 min and the reaction was stopped by boiling for 3 min. The samples were centrifuged for 5 min in a bench top centrifuge at the top speed and then assayed for AIs activity as described (Zhang, 1993). Blue colony indicates the presence of AI that activates the lacZ reporter gene, and white colony indicates absence of AI. Rows from left to right: 1, OHHL control without protein extract; 2-7, samples after 10, 20, 30, 40, 50, 60 min enzyme reaction.

The present invention is based on the discovery that the SEQ ID NO:2 protein has the effect of reducing or eliminating the activity of bacterial autoinducers (AIs). Consequently, the protein, and any nucleic acid that encodes the protein, may be used in a variety of situations where it is desired to reduce or eliminate the effect of such bacteria.

In one preferred aspect, the present invention provides a nucleic acid molecule which is selected from the group consisting of:
  a) a nucleic acid having the sequence of SEQ ID NO:1;
  b) a nucleic acid encoding the amino acid sequence of SEQ ID NO:2; and
  c) a nucleic acid that hybridizes to a) or b) above, wherein a positive hybridization signal is observed after washing with 1×SSC and 0.1% SDS at 55° C. for one hour. The nucleic acid optionally further comprises a signal peptide coding region of any sequence.

The nucleic acid sequence may be used to confer bacterial resistance in plants or animals. A nucleic acid that encodes a bacterial autoinducer inactivation protein can be introduced into a cell such that the inactivation protein is expressed by the plant or animal.

The nucleic acid sequence may be used to confer resistance to diseases where the expression of pathogenic genes are regulated by autoinducers, such as the diseases caused by *Pseudomonas aeruginosa*, *Erwinia stewartii*, *Xenorhabdus nematophilus*, *Erwinia chrysanthemi*, *Pseudomonas solanacerum*, and *Xanthomonas campestris* (Passador, et al., 1993; Pirhonen, et al., 1993; Pearson, et al., 1994; Beck von Bodman and Farrand, 1995; Barber, et al., 1997; Clough, et al., 1997; Costa and Loper, 1997; Dunphy, et al., 1997; Nasser, et al., 1998). Preferably, in the agricultural setting, the sequence may be used to confer soft rot disease resistance in susceptible plants, such as potato, eggplant, Chinese cabbage, carrot and celery.

The sequence may be introduced into plant or animal cells by well-known methods. Methods for the transformation or transfection of eukaryotic cells with exogenous nucleic acid sequences include transfection, projectile bombardment, electroporation or infection by *Agrobacterium tumefaciens*. These methods are likewise familiar to the person skilled in the area of molecular biology and biotechnology and need not be explained here in detail. As pathogenic bacteria cells are confined to the intercellular area of plant tissues, it is desirable to target the AiiA protein into the intercellular spaces. Such may be accomplished by fusing a secretion signal peptide to the AiiA protein (Sato, et al., 1995; Firek, et al., 1993; Conrad and Fiedler, 1998; Borisjuk, et al., 1999). Alternatively, a plant membrane attachment motif can be incorporated into the peptide sequence of AiiA for anchoring the AiiA enzyme in the outer surface of plant cell membrane.

The present invention provides a new strategy for engineering resistance to diseases. In particular, this strategy targets N-acyl homoserine lactone autoinducers that induce expression of pathogenic genes of many bacterial pathogens at a threshold concentration. This strategy is applicable to all plant, animal or mammal diseases where the expression of pathogenic genes of the bacterial pathogens is inducible by N-acyl homoserine lactone autoinducers.

The present invention also contemplates usage of a bacterial autoinducer inactivation protein directly to treat or prevent bacterial damage. For example, the protein may be applied directly to plants in need of such treatment or prevention. In a preferred embodiment, the protein is applied in the form of a composition which comprises an effective amount of the protein and a suitable carrier. The composition may have a wide variety of forms, including solutions, powders, emulsions, dispersions, pastes, aerosols, etc.

The bacterial autoinducer inactivation protein may also be used to treat bacterial infections in animals, including humans. In that application, an effective amount of the active ingredient is administered to an animal in need of such treatment.

For therapeutic treatment, the active ingredient may be formulated into a pharmaceutical composition, which may include, in addition to an effective amount of the active ingredient, pharmaceutically acceptable carriers, diluents, buffers, preservatives, surface active agents, and the like. Compositions may also include one or more other active ingredients if necessary or desirable.

The pharmaceutical compositions of the present invention may be administered in a number of ways as will be apparent to one of ordinary skill in the art. Administration may be done topically, orally, by inhalation, or parenterally, for example.

Topical formulations may include ointments, lotions, creams, gels, drops, suppositories, sprays, liquids and powders. Oral formulations include powders, granules, suspensions or solution in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen will depend on a number of factors which may readily be determined, such as severity and responsiveness of the condition to be treated.

Aspects of the invention will now be illustrated with reference to the following non-limiting examples.

EXAMPLE 1

Bacterial isolate 240B1 was isolated from soil suspension based on its function for inactivation of N-β-oxo-hexanoyl-L-homoserine lactone (OHHL) and N-β-oxooctanoyl-L-homoserine lactone (OOHL) and N-β-oxodecanoyl-L-homoserine lactone (ODHL) (Zhang, et al., 1993). Unless otherwise stated, OHHL was used for routine bioassay. *Erwinia carotovora* strain SCG1 was isolated from Chinese cabbage leaf showing soft rot symptoms. It has been confirmed that strain SCG1 produces AIs and elicits soft rot disease in potato and Chinese cabbage. *Escherichia coli* strain DH5α was used as a host for DNA cloning and subcloning. *Agrobacterium tumefaciens* strain NT1 (traR; tra::lacZ749) was used as an indicator in bioassay for AI activity (Piper, et al., 1993). *E. coli* strain was cultured in Luria-Bertani (LB) medium at 37° C. and other strains were cultured in LB (Miller, 1972) or YEB medium (per liter contains: casein hydrolysate 10 g, yeast extract 5 g, NaCl 10 g, sucrose 5 g, $MgSO_4.7H_2O$ 0.5 g, agar 15 g, pH 7.2) at 28° C. The minimal salts medium with mannitol and $(NH4)_2SO_4$ as carbon and nitrogen sources was used for bioassay of OHHL (Petit and Tempe, 1978). Appropriate antibiotics were added as indicated at the following concentrations: ampicillin, 100 μg/ml; tetracycline, 20 μg/ml and kanamycin, 50 μg/ml.

Bioassay of AIs Activity

The qualitative and quantitative bioassay methods for determination of AIs activity has been described previously (Zhang, 1993). For determination of the AIs production ability of wild-type and genetically modified *Erwinia* strains, the same bioassay procedure was used except that no OHHL was added into the bacterial culture.

Cloning and Sequencing of the AiiA Gene

Genomic DNA from 240B1 was digested partially with EcoRI. DNA fragments were ligated to the dephosphorylated EcoRI site of cosmid vector pLAFR3 (Staskawicz, et al., 1987). Ligated DNA was packaged with Gigapack III XL Packaging Extract (Stratagene) and transfected into *E. coli* DH5α. Cosmid clones with OHHL inactivation activity were identified by using the bioassay method described above. Subcloning into sequencing vector pGEM-7Zf(+) was carried out by routine techniques (Sambrook, et al., 1989). Deletion analysis was carried out by using DnaseI method as described by Lin, et al. (1985). The sequencing was performed on both strands using the ABI PRISM™ dRhodamine Terminator Cycle Sequencing Ready Reaction Kit (PE Applied Biosystems). Nucleic acid sequence data and deduced amino acid sequences were analyzed with a DNASTAR™ sequence analysis software package (DNAS- TAR Inc.) and database searches were performed using the BLASTA search algorithm (Altschul, et al., 1990).

Genetic Modification of *Erwinia* Strain SCG1

The E7-R3 plasmid, carrying the aiiA gene in the cosmid vector pLAFR3, was transferred into *Erwinia* stain SCG1 by triparental mating with the helper strain RK2013 (Ditta, et al., 1980). Transconjugants were selected on the plates containing minimal medium with tetracycline and confirmed by PCR with primers specific to the aiiA gene.

Virulence Tests

The virulence of wild-type *Erw. carolovora* strain SCG1 and the aiiA gene transformant SCG1 (E7-R3) was evaluated by inoculation. Four μl of early stationary phase bacterial suspension (containing ~$2\times10^9$ cell/ml) or diluted bacteria was added to the cut surfaces or wounding sites of plant tissues. The inoculated plant tissues were incubated in a Petri dish at 28° C. overnight. The severity of soft rot was examined 48 hours after incubation.

Results

Screening of Bacteria that Inactivate AIs

Bacterial isolates from plant and soil samples were screened for enzymatic inactivation of AIs. A bacterial isolate 240B1, which showed a strong ability to eliminate AIs activity, was selected for further study. The total protein extracts from isolate 240B1 eliminated AIs activity completely during one-hour incubation (FIG. 1), and the capacity of the protein extract to inactivate AIs was abolished by treatment with proteinase K for 1 hour or boiling for 5 min. These observations indicate enzymatic inactivation of AIs by bacterial isolate 240B1. The isolate was taxonomically characterized as *Bacillus* sp., because of the following characteristics: Gram-positive, rod-shaped, catalase positive, facultatively anaerobic, and 16 rRNA sequence homology to that of other *Bacillus* bacteria (data not shown).

Figure 2:
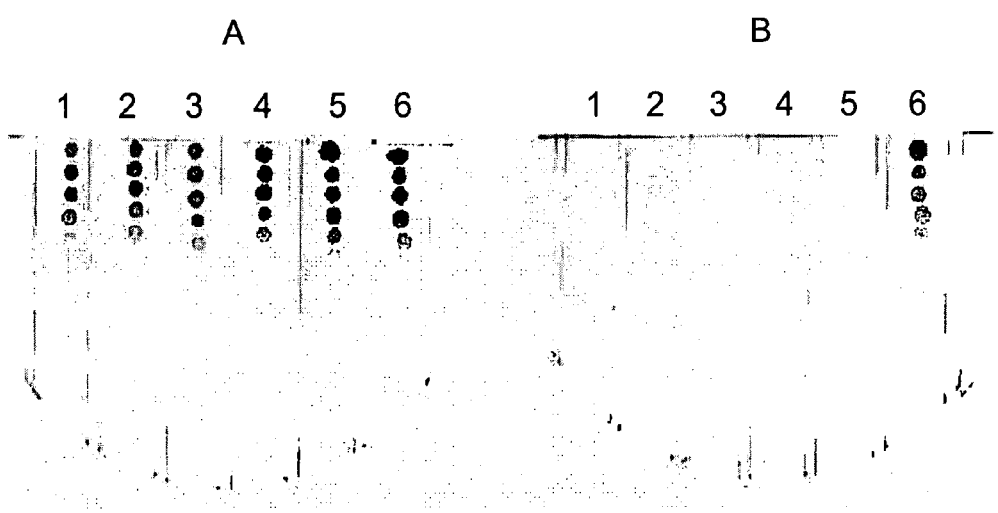
FIG. 2 shows the estimation of molecular mass of AIs inactivation enzyme. A 600 µl aliquot of cell extracts was added to the Centricon 30 (Amicon) and was centrifuged at a speed of 5000×g for 30 min at 4° C. Passing fraction (550 microliters) and un-passing fraction (50 microliters) were topped up separately to a final volume of 600 microliters by adding 0.2 M phosphate buffer (pH 7.0). For bioassay, different amounts of protein samples were added to the tubes containing OHHL in a final concentration of 20 µM. From row 1 to 6, protein samples added were 2, 4, 6, 8, 10 and 0 ul and the final reaction volume was 20 microliters for each reaction. Plate A: Passing fraction, Plate B: un-passing fraction.

The molecular mass of the enzyme for AIs inactivation appears to be larger than 30 kDa. Its activity was lost after passing the protein extract through Centricon 30 (Amicon) but the activity was recovered in the re-suspended fraction that failed to pass the Centricon 30 (FIG. 2).

Cloning and Localization of AIs Inactivation Region

Figure 3:
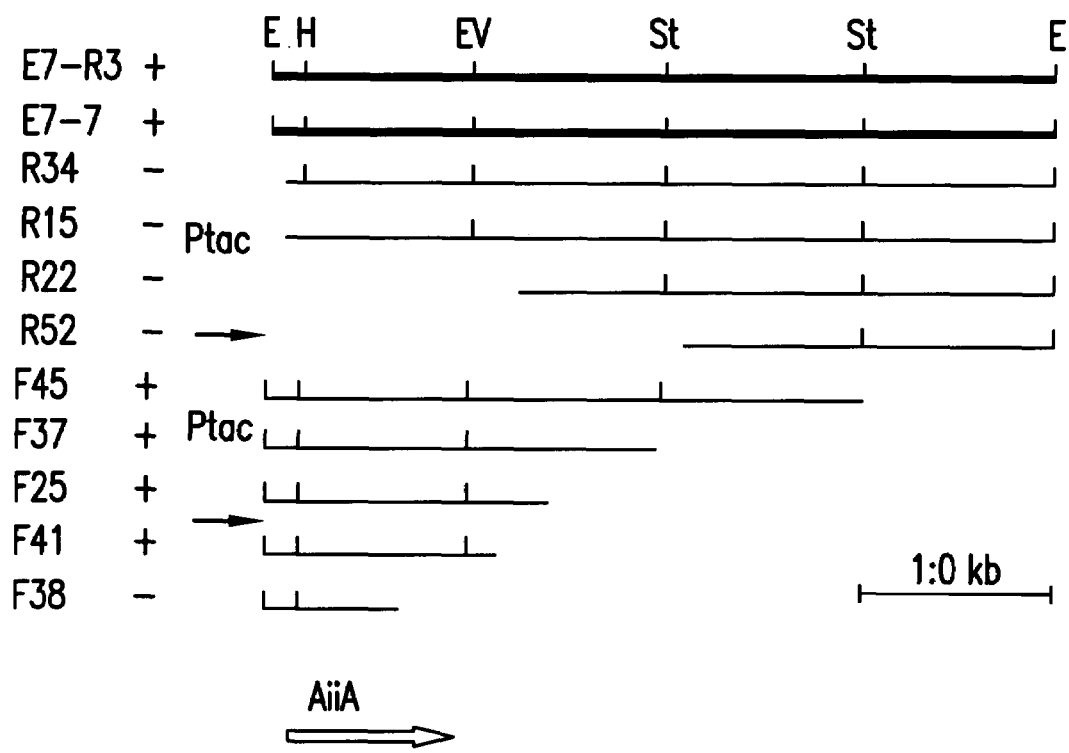
FIG. 3 shows the cloning and deletion analysis of *Bacillus* SP. strain 240B1 AI inactivation region. Cosmid clone E7-R3 contains the 4.3-kb EcoRI fragment identified by restriction analysis of overlapping cosmid clones. For deletion analysis, the same fragment was cloned into cloning vector pGEM-7Zf(+) for generation of clone E7-7. The deletion subclones were produced by restriction enzyme digestion and Dnase I treatment from the clone E7-7. The location and direction of Ptac promoters in the cosmid and in the pGEM-7Zf(+) clone are indicated by arrows. AI inactivation activity of the clones is shown in the second column: +, with AI inactivation activity; -, without AI inactivation activity. Restriction enzymes: E, EcoRI; H, HindIII; Ev, EcoRV; St, StyI. The location and direction of transcription of the aiiA ORF is indicated by an open arrow.

To identify the gene encoding AIs inactivation, a cosmid library was constructed with the genomic DNA of *Listera* sp. strain 240B1. Twelve hundred clones were screened for AIs inactivation activity. Three clones showing AIs inactivating function were identified. Restriction analysis showed that the 3 clones shared one common band of 4.3-kb generated by EcoRI digestion. The bioassay with the subclone E7-7 containing this 4.3-kb EcoRI fragment confirmed that this fragment encodes AIs inactivation function (FIG. 3). To identify the minimum size and the location of the AIs inactivation gene (aiiA), a serial of deletion clones was generated by deletion from both ends of this 4.3-kb fragment with the DNaseI method (Lin, et al., 1985). The results indicated that the aiiA gene is contained in a 1.2 Kb fragment in clone F41 (FIG. 3).

AiiA Gene Encodes a Novel Protein

The 1.2-kb DNA insert in clone F41 was completely sequenced from both strands. The nucleotide sequence of aiiA and the predicted amino acid sequence are shown in FIG. 4. The complete sequence of the DNA insert contains 1,222 base pairs and there are 4 potential in-frame open reading frames (ORF) starting from nucleotide position of 1, 42, 156 and 228 respectively (FIG. 4). Deletion analysis indicated that only the longest ORF encodes AIs inactivation function, because the clone R34, in which the 48 bp promoter region and nucleotides from 1 to 13 in the longest ORF were deleted, lost AI inactivation function completely, although the remaining DNA insert was placed under the control of a functional Ptac promoter (FIG. 3). This is confirmed by fusing the longest ORF to the glutathione S-transferase gene in the same ORF and testing for AI inactivation activity of the purified fusion protein (data not shown). This ORF contains 750 bp nucleotide and encodes a protein of 250 amino acids, with a predicted molecular mass of 28,036 daltons and an isoelectric point at 4.7, because of 19 strongly basic and 39 strongly acidic amino acids residues. The putative initiation codon is preceded at a spacing of 7 bp by a potential ribosome-binding sequence (AAGGTGG) which is complementary to the 3' end of the *E. coli* 16S rRNA. The best sequence match (TATTGT) to the consensus −10 promoter element (TATAAT) occurs 35 bp upstream of the initiation codon. A TCTT box following a T-rich region resembling the potential factor-independent termination site is found downstream of the termination codon (Brendel, 1986). The total GC content of the aiiA gene is 37% and GC content in the third position of the codon is 27.2%.

Database searches showed that the aiiA gene has no significant similarity to known sequences in the major databases (GenBank, European Molecular Biology Laboratory, Protein Information Resources, and Swiss-Prot) by FASTA and BLAST analysis of either nucleotide or peptide sequence level, suggesting that AiiA is a novel protein. Consensus protein motif search using the Genetics Computer Group (Madison, Wis.) MOTIF program showed that a short peptide sequence, "ILVDTGMPESAV" (SEQ ID NO:3) from position 47 to 58 in AiiA, is similar but not identical to the aspartyl protein active site signature pattern (Rawlings and Barrett, 1995) (FIG. 5).

Figure 6:
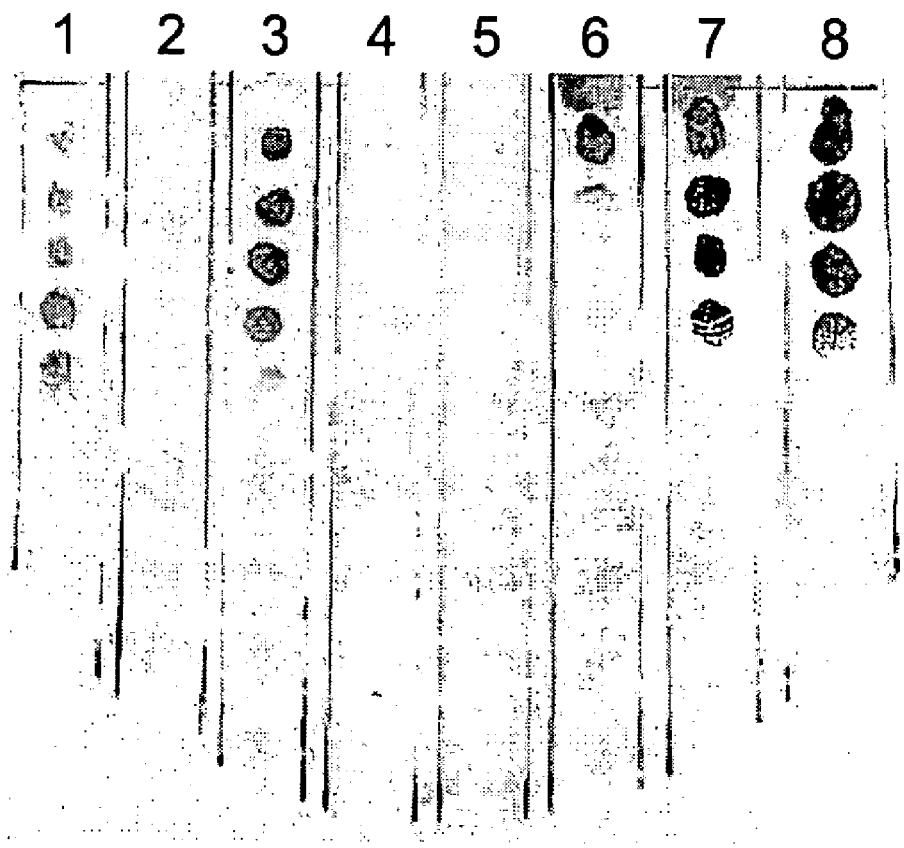
FIG. 6 shows the bioassay for AIs inactivation activities in *Bacillus* sp. strain 240B1, *E. coli* clones and AIs production activity in *Erwinia carotovora* strains. Row 1, OHHL control; row 2, *Bacillus* sp. strain 240BI; row 3, *E. coli* DH5a; row 4, *E. coli* DH5a (pE7-R3); row 5, *E. coli* DH5α (pF41); row 6, *Erw. carotovora* SCG1 (pE7R3); row 7, *Erw. carotovora* SCG1 (pLAFR3); row 8, *Erw. carotovora* SCG1. In the bioassay, OHHL was added to a final concentration of 20 µM to the samples from lines 1 to 5. No exogenous AIs were added to the samples from rows 6 to 8.

Expression of aiiA Gene in *Erwinia carotovora* Decreases AIs Releasing and Attenuates Virulence The cosmid clone E7-R3 was transferred into *Erwinia carotovora* strain SCG1 by triparental mating. The pLAFR3 vector has been safely maintained in *Erwinia carotovora* without selection pressure. The bioassay showed that the AIs released by *Erwinia carotovora* (E7-R3) was significantly reduced (FIG. 6, lane 6), while the presence of the cosmid vector pLAFR3 alone in *Erwinia carotovora* did not affect AIs production (FIG. 6, lanes 7). Data suggest that the most of AIs produced by *Erwinia carotovora* strain SCG1 was inactivated by aiiA gene product.

Figure 7:
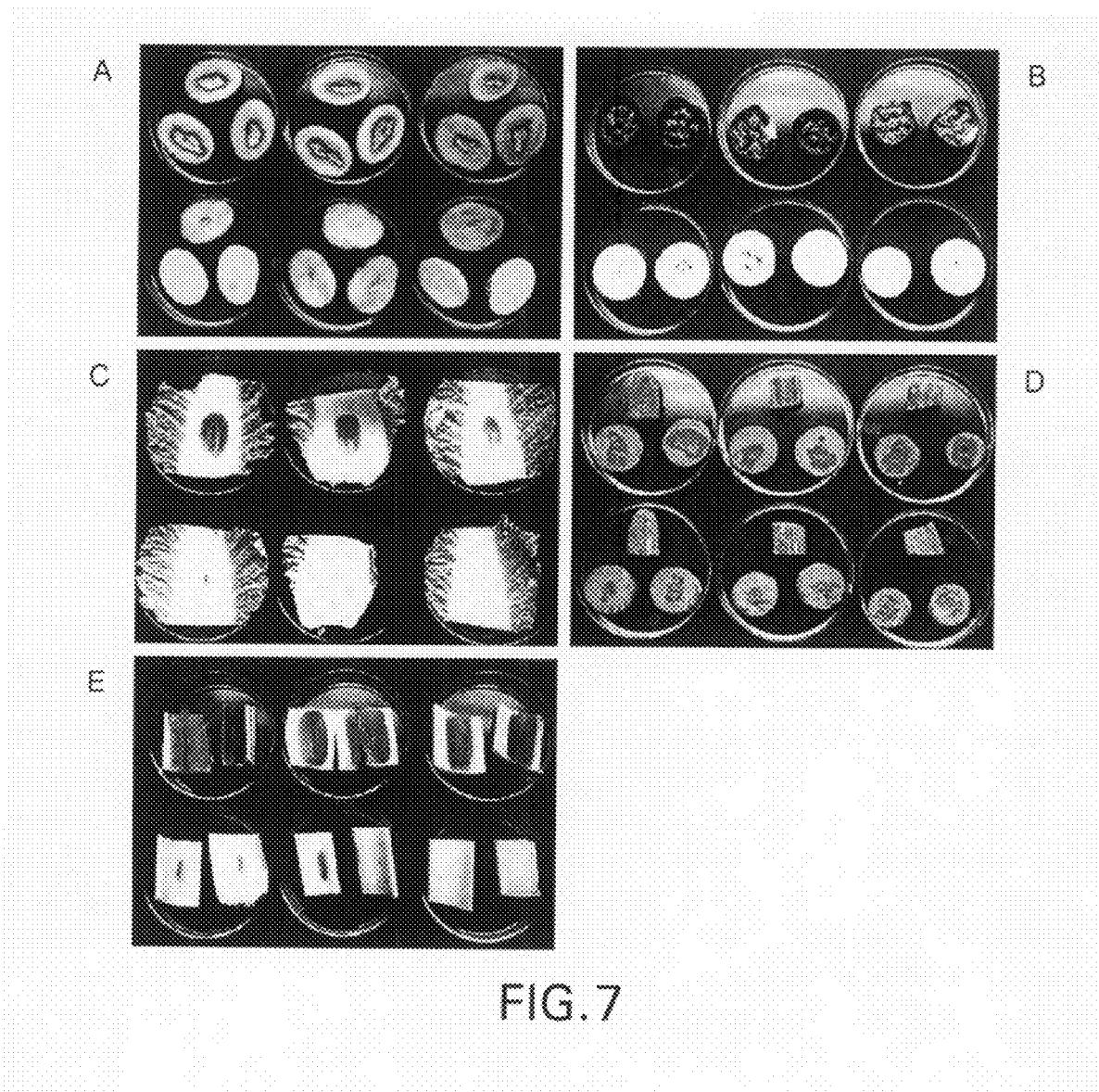
FIG. 7 shows the effect of aiiA gene expression in *Erw. carotovora* on pathogenicity in (A), potato; (B), eggplant; (C), Chinese cabbage; (D), carrot; and (E), celery. Top: plant tissues were inoculated with *Erw. carotovora* SCG1. Bottom: plant tissues were inoculated with *Erw. carotovora* SCG1 (pE7-R3). The actively growing bacteria were centrifuged for 1 min at 3000×g, resuspended with YEB liquid medium to OD600=1.3 ($2\times10^9$ cfu/ml) which was designed as $10^0$ inoculum. The $10^0$ inoculum was diluted 5 and 10 times respectively to prepare $10^{-1/2}$ and $10^{-1}$ dilutions. The Plant tissues were inoculated by adding a 4-µl volume of bacteria inoculum to the freshly cut surface or a wounding site punched by a pipette tip. The inoculum concentration from the left to the right plate: $10^0$; $10^{-1/2}$; and $10^{-1}$. The inoculated plant tissues were placed in plastic plates and incubated at 28° C. The photograph was taken 48 h after inoculation.

The *Erwinia carotovora* SCG1 (E7-R3) that expresses AiiA protein failed to or caused only minor soft rot disease symptom in potato, eggplant, Chinese cabbage, carrot and celery, while its parental strain caused severe symptoms (FIG. 7A, B, C, D, E). To prevent experimental errors due to genetic variations, four colonies from *Erwinia carotovora* strain SCG1 and its aiiA gene transformants respectively, were randomly selected for testing AIs production and virulence on potato. Similar results were obtained in both experiments. The *Erwinia carotovora* strain SCG1 (pLAFR3) that contains the cosmid vector only caused the same level of disease severity as its parental strain *Erwinia carotovora* strain SCG1 (FIG. 7F).

Discussion

Bacterial isolate 240B I, which was identified as *Bacillus* sp., produces an enzyme that can effectively inactivate the three AIs tested, i.e., N-β-oxo-hexanoyl-L-homoserine lactone, N-β-oxo-octanoyl-L-homoserine lactone and N-β-oxo-decanoyl-L-homoserine lactone. The gene (aiiA)

encoding the AI inactivation enzyme has been cloned and fully sequenced. Expression of the aiiA gene in transformed *E. coli* and pathogenic bacteria *Erwinia carolovora* confers ability for AI inactivation and significantly reduces the AIs release from *Erwinia carolovora*. To our knowledge, it is the first protein identified capable of enzymatic inactivation of N-acyl-homoserine lactones, the autoinducers for global gene regulation in a diverse of bacteria species.

The AiiA is a novel protein. There is no significant homology to known proteins in major databases. It shares similarities to the consensus pattern of the aspartyl proteases active site (Rawlings and Barret, 1995). Aspartyl proteases, also known as acid proteases, are widely distributed in vertebrates, fungi, plants, retroviruses and some plant viruses. The aspartyl proteases from most retroviruses and some plant viruses are homodimers. The molecular mass of AiiA protein is about 28 kDa but it failed to pass a molecular sieve with a cut off size of 30 kDa, indicating a possibility that AiiA protein exists as a homodimer or homomultimer under the natural conditions. However, there is also a possibility that AiiA monomer has an irregular three-dimensional structure, which hinders it passing through the molecular sieve. Aspartyl proteases are endopeptidases and hydrolyses amide linkages of proteins. Crystallographic study has shown that the enzyme of the aspartyl protease family are bilobed molecules with the active-site cleft located between the lobes, and each lobe contributing one of the pair of aspartic acid residues that is responsible for the catalytic activity (Sielecki et al., 1991).

*Erwinia carotovora* is a plant pathogen that produces and secretes exoenzymes that act as virulence determinants for soft rot diseases of various plants including potato, cabbages, tomato, chili, carrot, celery, onion, and lettuce (Kotoujansky, 1987).

Mutants that were defective in the producing N-3-(oxo-hexanoyl)-L-homoserine lactone were also defective in synthesis of the pectinase, cellulase and protease exoemzymes. These mutants failed to induce soft rot disease in potato tubers (Jones, et al., 1993). It was found that the expI gene, which is homologous to luxI gene of *Vibrio fischeri*, encodes autoinducer production in *Erwinia carotovora*. The expi mutant was avirulent when it was inoculated to tobacco leaf but the virulence was restored by external autoinducer addition (Pirhonen, et al., 1993). Obviously, autoinducers are a potential target for genetic engineering of plant soft rot disease resistance. As an interim test and a concept proving approach, the cosmid clone containing the aiiA gene was introduced to *Erwinia carotovora* strain SCG1. Expression of the AiiA enzyme in *Erwinia carotovora* significantly reduced the release of autoinducers, and the genetically modified *Erwinia carotovora* that expressed AiiA failed to induce any or induce only minor soft rot disease symptom on all plants tested, including potato, eggplant, Chinese cabbage, carrot and celery. Our results further support the important role of autoinducers in the regulation of expression of virulence genes in *Erwinia carotovora*, and the potential of the aiiA gene to confer resistance to soft rot disease and other diseases in which the autoinducers are involved in regulation of pathogenic gene expression.

The present invention provides a new strategy for engineering resistance to diseases. In particular, this strategy targets N-acyl homoserine lactone autoinducers that induce expression of pathogenic genes of many bacterial pathogens at a threshold concentration. By using the above-mentioned conception-proving approach, the present invention demonstrates that reduction or elimination of autoinducers produced by pathogenic bacteria by an autoinducer inactivation enzyme significantly attenuates pathogenicity of otherwise virulent bacterial pathogen. Because the expression of pathogenic genes in pathogenic bacteria requires a threshold concentration, this AI-inactivation strategy is applicable to all plant, animal or mammal diseases where the expression of pathogenic genes of the bacterial pathogens is inducible by N-acyl homoserine lactone autoinducers.

The aiiA gene could also be a useful tool for investigation of the role of AIs in those bacteria where the biological functions regulated by AIs has not been established. In recent years, many more bacteria species have been shown to produce AIs (Bassler, et al., 1997; Dumenyo, et al., 1998; Cha, et al., 1998; Surette, et al., 1999). Some of them are important plant pathogens such as *Psendomonas* and *Xanthomonas* species. The gene knock out approach based on sequence homology could be difficult. The overall levels of sequence similarity of AIs synthase and the related regulatory protein from different genera are rather low, often no higher than 28-35% identity between LuxI-type proteins and 18-25% identity for LuxR-type proteins (Fuqua et al., 1996). However, it is feasible and simple to introduce the aiiA gene into these bacteria to probe the biological functions regulated by AIs.

REFERENCES

Allison, D. G. R., B. Sanjose, C. Jaspe, A. Gilbert, P. (1998). Extracellular products as mediators of the formation and detachment of *Pseudomonas fluorescens* biofilms. FEMS Microbiology Letters 167, 179-184.

Altschul, S. F., Gish, W., Miller, W., Myers, E. W., and Lipman, D. J. (1990). Basic local alignment search tool. *Journal Molecular Biology* 215, 403-410.

Barber, C. E., Tang, J. L., Feng, J. X., Pan, M. Q., Wilson, T. J., Slater, H., Dow, J. M., Williams, P., and Daniels, M. J. (1997). A novel regulatory system required for pathogenicity of *Xanthomonas campestris* is mediated by a small diffusible signal molecule. *Molecular Microbiology* 24, 555-566.

Bassler, B. L., Greenberg, E. P. & Stevens, A. M. (1997). Cross-species induction of luminescence in the quorum-sensing bacterium *Vibrio harveyi*. *Journal of Bacteriology* 179, 4043-4045.

Beck von Bodman, S., and Farrand, S. K. (1995). Capsular polysaccharide biosynthesis and pathogenicity in *Erwinia stewartii* require induction by an Nacylhomoserine lactone autoinducer. Journal of Bacteriology 177, 5000-5008.

Borisjuk, N. V., Borisjuk, L. G., Logendra, S., Logendra, S., Petersen, F., Gleba, Y., Raskin, I. 1999. Production of recombinant proteins in plant root exudates. *Nature Biotechnology* 17, 466-469.

Brendel, V., and Trifonov, E. N. (1984). A computer algorithm for testing potential prokaryotic terminators. *Nucleic Acids Research* 12, 4411-4427.

Cao, J. G., and Meighen, E. A. (1989). Purification and structural identification of an autoinducer for the luminescence system of *Vibrio harveyi*. *Journal of Biological Chemistry* 264, 21670-21676.

Cha, C., Gao, P., Chen, Y. C., Shaw, P. D., and Farrand, S. K. (1998). Production of acyl-homoserine lactone quorum-sensing signals by gram-negative plant associated bacteria. *Molecular and Plant Microbe Interactions* 11, 1119-1129.

Choi S. H., Greenberg E. P. (1991). The C-terminal region of the *Vibrio fischeri* LuxR protein contains an inducerindependent lux gene activating domain. *Proc. Natl. Acad. Sci. USA* 88, 11115-11119.

Choi S. H, Greenberg E. P. (1992). Genetic evidence for multimerization of LuxR, the transcriptional activator of *Vibrio fischeri* luminescence. *Molec. Mar. Biol. Biotech.* 1: 408-413.

Clough, S. J., Lee, K. E., Schell, M. A., and Denny, T. P. (1997). A two-component system in *Ralstonia (Pseudomonas) solanacearum* modulates production of PhcA regulated virulence factors in response to 3-hydroxypalmitic acid methyl ester. *J Bacteriol* 179, 3639-3648.

Collmer, A. K., N. T. (1986). The role of pectic enzymes in plant pathogenesis. *Annual Review of Phytopathology* 24, 383-409.

Conrad, U., and Fiedler, U. 1998. Compartment-specific accumulation of recombinant immunoglobulins in plant cells: an essential tool for antibody production and immunomodulation of physiological functions and pathogen activity. *Plant Molecular Biology* 38, 101-109.

Costa, J. M. & Loper, J. E. (1997). EcbI and EcbR: homologs of LuxI and LuxR affecting antibiotic and exoenzyme production by *Erwinia carotovora* subsp. *betavasculorum*. *Can J Microbiol* 43, 1164-71.

Davies, D. G., Parsek, M. R., Pearson, J. P., Iglewski, B. H., Costerton, J. W., and Greenberg, E. P. 1998. The involvement of cell-to-cell signals in the development of a bacterial biofilm. *Science* 280, 295-298.

Ditta, G., StanFleld, S., Corbin, D., and Helinski, D. R. (1980). Broad host range DNA cloning system for gram-negative bacteria: construction of a gene bank of *Rhizobium meliloti*. *Proc Natl Acad Sci USA* 77, 7347-7351.

Dumenyo, C. K. M., A. Chun, W. Chatterjee, A K. (1998). Genetic and physiological evidence for the production of N-acyl homoserine lactones by *Pseudomonas syringae* pv. *syringae* and other fluorescent plant pathogenic *Pseudomonas* species. *European Journal of Plant Pathology* 104(6). 1998.569-582. 104, 569-582.

Dunphy, G., Miyamoto, C., and Meighen, E. (1997). A homoserine lactone autoinducer regulates virulence of an insect-pathogenic bacterium, *Xenorhabdus nematophilus* (Enterobacteriaceae). *J. Bacteriol.* 179, 5288-5291.

Eberhard, A., Burlingame, A. L., Eberhard, C., Kenyon, G. L., Nealson, K. H., and Oppenheimer, N. J. (1981). Structural identification of autoinducer of *Phoptobacterium fischeri* luciferase. *Biochemistry* 20, 2444-2449.

Eberl, L., Winson, M. K., Sternberg, C., Stewart, G. S. A. B., Christiansen, G., Chhabra, S. R., Bycroft, B., Williams, P., Molin, S. & Givskov, M. (1996). Involvement of N-acyl-L-homoserine lactone autoinducers in controlling the multicellular behaviour of *Serratia liquefaciens*. *Molecular Microbiology* 20, 127-136.

Firek, S., Draper, J., Owen M. R. L., Gandecha, A., Cockburn, B., and Whitelam, G. C. 1993. Secretion of a functional single-chain Fv protein in transgenic tobacco plants and cell suspension cultures. *Plant Molecular Biology* 23, 861-870.

Fuqua C, Winans S. C. (1996). Conserved cis-acting promoter elements are required for density-dependent transcription of *Agrobacterium tumefaciens* conjugal transfer genes. *J. Bacteriol.* 178, 435-440.

Fuqua W. C., Winans S. C., Greenberg E. P. (1994). Quorum sensing in bacteria: the LuxR/LuxI family of cell density-responsive transcriptional regulators. *J. Bacteriol.* 176, 269-75.

Fuqua, C., Winans, S. C., and Greenberg, E. P. (1996). Census and consensus in bacterial ecosystems: The LuxR-LuxI family of quorum-sensing transcriptional regulators. *Annu. Rev. Microbiol.* 50, 727-751.

Hanzelka, B. L., Greenberg, E. P. (1995). Evidence that the N-terminal region of the *Vibrio fischeri* LuxR protein constitutes an autoinducer-binding domain. *J. Bacteriol.* 177, 815-817.

Jones, S. M., Yu, B., Bainton, N. J., Birdsall, M., Bycroft, B. W., Chhabra, S. R., Cox, A. J. R., Golby, P., Reeves, P. J., Stephens, S., Winson, M. K., Salmond, G. P. C., Stewart, G. S. A. B., and Williams, P. (1993). The Lux autoinducer regulates the production of exoenzyme virulence determination in *Erwinia carotovora* and *Pseudomonas aeruginosa*. *EMBO J.* 12, 2477-2482.

Kotoujansky, A. (1987). Molecular genetics of pathogenesis by soft-rot Erwinias. *Annual Review of Phytopathology* 25, 405-430.

Lin, H. C., Lei, S. P., and Wilcox, G. (1985). An improved DNA sequencing strategy. *Anal Biochem* 147, 114-119.

Meighen, E. A. (1994). Genetics of bacterial luminescence. *Annu. Rev. Genet.* 28, 117-139.

More, M. I., Finger, L. D., Stryker, J. L., Fuqua, C., Eberhard, A. & Winans, S. C. (1996). Enzymatic synthesis of a quorum-sensing autoinducer through use of defined substrates. *Science* 272, 1655-1658.

Nasser, W., Bouillant, M. L., Salmond, G. & Reverchon, S. (1998). Characterization of the *Erwinia chrysanthemi* expl-expR locus directing the synthesis of two N-acyl-homoserine lactone signal molecules. *Molecular Microbiology* 29, 1391-1405.

Passador, L., Cook, J. M., Gambello, M. J., Rust, L., Iglewski, B. H. (1993). Expression of *Pseudomonas aeruginosa* virulence genes requires cell-to-cell communication. *Science* 260, 1127-1130.

Pearson, J. P., Gray, K. M., Passador, L., Tucker, K. D., Eberhard, A., Iglewski, B. H., and Greenberg, E. P. (1994). Structure of the autoinducer required for expression of *Pseudomonas aeruginosa* virulence genes. *Proc Natl Acad Sci USA* 91, 197-201.

Petit, A., and Tempe, J. (1978). Isolation of *Agrobacterium* Ti plasmid regulatory mutants. *Mol. Gen. Genet.* 167, 147-155.

Pierson, L. S., 3rd, Keppenne, V. D., and Wood, D. W. (1994). Phenazine antibiotic biosynthesis in *Pseudomonas aureofaciens* 30-84 is regulated by PhzR in response to cell density. *J. Bacteriol.* 176, 3966-74.

Piper, K. R., Beck von Bodman, S., and Farrand, S. K. (1993). Conjugation factor of *Agrobacterium tumefaciens* regulates Ti plasmid transfer by autoinduction. *Nature* 362, 448-450.

Pirhonen, M., Flego, D., Heikinheimo, R., and Palva, E. (1993). A small diffusible signal molecule is responsible for the global control of virulence and exoenzyme production in the plant pathogen *Erwinia carotovora*. *EMBO J.* 12, 2467-2476.

Rawlings, N. D. B., A. J. (1995). Families of aspartic peptidases, and those of unknown catalytic mechanism. In *Methods in Enzymology*, pp. 105-180. Edited by A. J. Barrett. New York: Academic Press.

Sambrook, J. F., E. F. Maniatis, T. (1989). *Molecular Cloning*, Second edn. New York: Cold Spring Harbor Laboratory Press.

Sato, F., Koiwa, H., Sakai, Y., Yamada, Y. (1995). Synthesis and secretion of tobacco neutral PR-5 protein by transgenic tobacco and yeast. *Biochemical & Biophysical Research Communications.* 211, 909-913.

Schaefer, A. L. V., D L. Hanzelka, B L. Cronan, J E Jr. Greenberg, E P. (1996). Generation of cell-to-cell signals in quorum sensing: Acyl homoserine lactone synthase activity of a purified *Vibrio fischeri* LuxI protein. *Proceedings of the National Academy of Sciences of the United States of America* 93, 9505-9509.

Shadel, G. S., Young, R., Baldwin, T. O. (1990). Use of regulated cell lysis in a lethal genetic selection in *Escherichia coli*: identification of the autoinducer-binding region of the LuxR protein from *Vibrio fischeri* ATCC 7744. *J. Bacteriol.* 172, 39803987.

Sielecki, A. R., Fujinaga, M., Read, R. J. & James, M. N. (1991). Refined structure of porcine pepsinogen at 1.8 A resolution. *J Mol Biol* 219, 671-692.

Sitnikov, D., Schineller, J. B., Baldwin, T. O. (1995). Transcriptional regulation of bioluminescence genes from *Vibrio fischeri*. *Mol. Microbiol.* 17, 801-12.

Slock J, Kolibachuk D, Greenberg E P. (1990). Critical regions of the *Vibrio fischeri* LuxR protein defined by mutational analysis. J. Bacteriol. 172: 3974-3979.

Staskawicz, B. D., D. Keen, N. T. and Napoli, C. (1987). Molecular characterization of cloned avirulence genes from race 0 and race I of *Pseudomonas syringae* pv. *glycinea*. *Journal of Bacteriology* 169, 5789-5794.

Surette, M. G. B., B L. (1998). Quorum sensing in *Escherichia coli* and *Salmonella typhimurium*. *Proceedings of the National Academy of Sciences of the United States of America*. 95, 7046-7050.

Throup, J. P., Camara, M., Briggs, G. S., Winson, M. K., Chhabra, S. R., et al. (1995). Characterisation of the yenI/yenR locus from *Yersenia enterocolitica* mediating the synthesis of two N-acylhomoserine lactone signal molecules. *Mol. Microbiol.* 17, 345-356.

Zhang, L.-H. (1993). Molecular biology and biochemistry of a novel conjugation factor in *Agrobacterium*. Doctoral Dissertation, The Adelaide University, Australia.

Zhang, L.-H., Murphy, P. J., Kerr, A., and Tate, M. E. (1993). *Agrobacterium* conjugation and gene regulation by N-acyl-L-homoserine lactones. *Nature* 362, 446-447.

The invention claimed is:

1. An isolated nucleic acid molecule encoding a bacterial autoinducer inactivation protein, wherein the nucleic acid is selected from the group consisting of:
 a) the nucleic acid of SEQ ID NO:1; and
 b) a nucleic acid encoding the amino acid sequence of SEQ ID NO:2.

2. The nucleic acid molecule of claim 1, which further comprises a signal peptide coding region of any sequence.

3. An expression vector which comprises the nucleic acid molecule of claim 1, wherein the expression vector propagates in a prokaryotic or eukaryotic cell.

4. A cell of a prokaryote or eukaryote transformed or transfected with the expression vector of claim 3.

5. A method for increasing disease resistance in a plant, which method comprises introducing into a cell of said plant a nucleic acid encoding a bacterial autoinducer inactivation protein, wherein the nucleic acid is selected from the group consisting of:
 a) the nucleic acid of SEQ ID NO:1; and
 b) a nucleic acid encoding the amino acid sequence of SEQ ID NO:2.

6. The method of claim 5, wherein the nucleic acid further comprises a signal peptide coding region of any sequence.

7. The method of claim 5, wherein the nucleic acid further comprises a membrane attachment domain-coding region of any source.

8. The method of claim 5, wherein the plant is susceptible to bacterial soft rot disease.

9. The method of claim 8, wherein the plant is selected from the group consisting of potato, eggplant, Chinese cabbage, carrot and celery.

10. The method of claim 5, wherein the plant is susceptible to a bacterial disease in which the expression of a virulence gene is regulated by an N-acyl homoserine lactone autoinducer.

11. A method of reducing bacterial autoinducer activity in a plant, which method comprises introducing into a cell of said plant the nucleic acid molecule of claim 1.

* * * * *